United States Patent [19]

Hausman

[11] Patent Number: 4,640,912

[45] Date of Patent: Feb. 3, 1987

[54] ADMINISTRATION OF "ACTIVE" CHONDROITIN SULFATE A AND "ACTIVE" CHONDROITIN SULFATE C OR MIXTURES THEREOF TO MAMMALS INCLUDING HUMANS

[76] Inventor: Marvin S. Hausman, 124 Montana Ave., Santa Monica, Calif. 90403

[21] Appl. No.: 502,446

[22] Filed: Jun. 9, 1983

[51] Int. Cl.[4] ................ A61K 31/73; C08B 37/00
[52] U.S. Cl. .................................. 514/54; 536/54; 536/118
[58] Field of Search ............... 424/180; 536/118, 54; 514/54

[56] References Cited

U.S. PATENT DOCUMENTS

| | | | |
|---|---|---|---|
| 3,175,942 | 3/1965 | Anderson et al. | 536/118 |
| 4,105,760 | 8/1978 | Szejtli et al. | 536/118 |
| 4,302,577 | 11/1981 | Rucker | 536/118 |

FOREIGN PATENT DOCUMENTS 1305807  2/1973  United Kingdom ............... 536/118

*Primary Examiner*—Johnnie R. Brown
*Attorney, Agent, or Firm*—Joseph E. Mueth

[57] ABSTRACT

The administration of "active" chondroitin sulfate A (CSA), "active" chondroitin sulfate C (CSC), or mixtures thereof to mammals including humans suffering from cancer, bacterial infections, trauma, irritation, placement of foreign objects, tubes or instruments, or damage of the upper or lower urinary tract, and related transitional cell surfaces to prevent cancer cell implantation or adherence, bacterial infestation or adherence, trauma, irritation, or damage from placement of foreign objects, tubes or instruments in the kidney, renal pelvis, ureter, bladder, urethra and related transitional cell surfaces by the irrigation of said surfaces and/or tubes and instruments with a solution of said drugs or mixtures thereof.

6 Claims, No Drawings

ADMINISTRATION OF "ACTIVE" CHONDROITIN SULFATE A AND "ACTIVE" CHONDROITIN SULFATE C OR MIXTURES THEREOF TO MAMMALS INCLUDING HUMANS

BACKGROUND OF THE INVENTION

The use of "active" chondroitin sulfate A and C (CSA and CSC), and mixtures of these drugs are known for use in the treatment of a variety of cardiovascular diseases and as preventative therapy for these diseases. These drugs including their method of production are described in Morrison U.S. Pat. Nos. 3,895,106 and 3,894,107 issued July 15, 1975. An improved method for the production of these drugs is disclosed in Rucker U.S. patent application Ser. No. 82,045, filed Oct. 5, 1979, now abandoned, and Rucker U.S. Pat. No. 4,302,577.

It was subsequently discovered that CSA, CSC and mixtures thereof, have a unique and very different therapeutic use. This use addresses the problem of organ and tissue transplant rejection by the human host, and the somewhat similar problem relating to inanimate implants such as tooth implants, hip prosthesis, intraocular implant, heart valve, etc. Transplant and implant rejection phenomena is believed to be associated with the immune system of the body, physiologic inflammatory processes, surgical procedures, mechanical interactions or a combination thereof. The immune system or host defense system recognizes the transplanted or implanted material as foreign and produces antibodies and inflammatory cells which attack the object foreign to the human host. Surgical failure and physiologic failure may also be related to surgical and/or mechanical tissue damage, blood clot formation with decreased blood flow, etc.

In accordance with copending U.S. patent application Ser. No. 263,788, filed May 14, 1981, now abandoned, it has been found that CSA, CSC or mixtures of the drugs seem to significantly reduce the tendency of the human body to reject transplants and increase the acceptance of implants.

The coating of the foreign tissues or objects and/or host treatment with the drugs of this invention reduces rejection and may result in better acceptance of the transplant or implant by the surrounding tissues. The coating of surgical instruments also reduces direct tissue damage resulting from contact with these instruments. Likewise, the coating of indwelling catheters or needles will reduce mechanical damage to contiguous endothelial cells within the vascular channel.

It has now been discovered that when these drugs are applied to the surface of the urinary tract, such as the bladder and urethral surfaces, it significantly inhibits the development of bacterial infections and the implantation or incidence of cancer in these areas.

It is believed that this development represents a significant advance in this area of therapy.

SUMMARY OF THE INVENTION

Briefly, the present invention comprises the administration of CSA, CSC, or mixtures thereof to manmals including humans suffering from cancer, bacterial infections, trauma, irritation, placement of foreign objects, tubes or instruments, damage of the upper or lower urinary tract, and related transitional cell surfaces to prevent cancer cell implantation or adherence, bacterial infestation or adherence, trauma, irritation, or damage from placement of foreign objects, tubes, or instruments to the kidney, renal pelvis, ureter, bladder, urethra and related transitional cell surfaces by the irrigation of said surfaces and/or tubes and instruments with a solution of said drugs or mixtures thereof.

It is an object of this invention to provide novel therapy in the prevention of cancer cell implantation, adherence or metastasis in the urinary tract.

It is also an object of this invention to provide novel therapy in the prevention of bacterial infection of the bladder and urinary tract.

It is also an object of this invention to provide novel therapy in the prevention of trauma, irritation or damage to the linings of the renal pelvis, ureter, bladder and urethra by indwelling catheters, tubes or foreign implants while also maintaining the patency of any of these tubular devices.

It is also an object of this invention to provide novel therapy in reducing mechanical damage to the transitional cell lining of the urinary tract by foreign bodies inserted into the kidney, renal pelvis, ureter, bladder or urethra by replacing the mucin glycosoaminoglycan lining of these organs by the invention which is a surface active agent.

These and other advantages and objects of the invention will be apparent from the more detailed description which follows.

DESCRIPTION OF THE PREFERRED EMBODIMENTS

Materials and Methods

Preparation of Bacteria

Escherichia coli type 04 was accommodated to David medium (Difco Laboratories, Detroit, Mich.) by serial passage using 2.5% inocula (vol/vol) and incubation at 37 degrees centigrade (c) overnight. To label the organisms with 14C, a 2.5% inoculum (vol/vol) was added to fresh Davis medium containing 10 micro curies of [14C] bicarbonate (Amersham/Searle, Des Plaines, Ill.) per ml, and the mixture was incubated overnight at 37 degrees C. The next morning the bacteria were spun in a centrifuge at 3,000 X g for 5 minutes and washed once with an equal volume of 0.9% NaCl (physiological saline solution; PSS). After washing, the bacteria were suspended in the respective solutions as described in step 3 in a total volume that was 10% of their original. For the control rabbits (step 2a), the suspension was placed into a solution containing 0. 1 M sodium phosphate monobasic (adjusted to pH 5.5 with sodium phosphate dibasic). This buffered solution (BS) was the basic one used for all the experiments described in step 3.

Basic Model

Male New Zealand White rabbits weighing 2 to 3 kg. were used. All animals were anesthetized with pentobarbital, 18 mg/kg of body weight.

Step 1: Urethral Catheter

Each rabbit was secured and given 100 ml of PSS intravenously over a 30-min. period. The intravenous infusion was turned off. A pediatric feeding tube no. 8 French (C.R. Bard, Murray Hill, N.J.) was inserted into the urethra and secured with a 4-0 silk purse-string tied around the penis. The abdomen was opened prior to step 2 to expose the bladder. Only in this fashion could one be assured of totally emptying the bladder of its contents between rinses or treatments. Between treatments the bladder was returned to the abdomen and the overlying fascia was secured.

Step 2: Preparation of Bladder (a) Control rabbits: The bladder was flushed through the catheter with four aliquots of 15 ml of PSS.

(b) Acid-treated bladders: Before the introduction of bacteria (step 3), the bladders of the animals which were to receive acid treatment (remove mucin layer) were flushed with four aliquots of 15 ml of PSS, after which they were slowly infused (over 20 sec.) with 7 ml of 0.6 N HCl through the catheter. When the acid had remained in the bladder for 60 seconds, it was aspirated and the bladder was flushed with one 15-ml aliquot of 0.5 M potassium phosphate dibasic (pH 9.4), followed by three additional rinsings with 15-ml aliquots of buffered saline (BS). The introduction of bacteria was then performed as in the basic model, step 3.

(c) CSA-treated bladders: The CSA preparation was made by adding powdered CSA to BS in a concentration of 50 mgm. per ml. The acid-treated bladders were infused with 5.0 ml of the CSA suspension and incubated for 30 min. The solution was then removed by aspiration and bacteria were instilled.

Step 3: Introduction of bacteria

All rabbits received 0.5 ml of BS followed immediately with 0.4 ml of bacteria as described in Preparation of Bacteria, and the catheter was clamped. Prior to addition of bacteria, the bladders were emptied of contents under direct vision.

when said surfaces are irrigated with an aqueous solution containing about 5% by weight of the drug.

Table II further summarizes the mean values of bacterial adherence in acid treated CSA treated bladders. The data shows that CSA can successfully recoat the bladder wall, thereby preventing bacterial adherence.

Data was analyzed using the Mann Whitney Rank Sum Test and Table III shows that the effect of CSA is statistically significant.

In general, the drug is used in an effective amount on the order of 1 to 20% by weight of an aqueous, saline or other irrigating solution used over a period of minutes, hours or days, and preferably administered by the urethral route or through any indwelling tube or instrument in the urinary tract.

In certain urologic surgical and/or diagnostic procedures, it is necessary to insert instruments such as cystoscopes, resectoscopes or catheters into the urinary tract. The patent invention can be beneficially used in such situations by introducing an irrigating solution of the drug through the instrument or catheter to aid in passage of these instruments or catheters as well as coating or lubricating the surface of these instruments or catheters and also in coating contiguous surfaces and thereby preventing trauma, irritation, bleeding, damage and possible infection. The invention can also be used as a lavage in endoscopy for removal of blood and tissue fragments as well as an irrigant to maintain the patency of instruments as well as an irrigant to maintain the patency of instruments or indwelling catheters used during or after urologic procedures.

The invention is generally useful for the irrigation of the upper and lower urinary tract surfaces to treat or

TABLE I

| | EFFECT OF CSA ON BACTERIAL ADHERENCE TO BLADDER MUCOSA AT 50 MG/ml | | | | | |
|---|---|---|---|---|---|---|
| | CONTROL | | CSA | | ACID CONTROL | |
| EXPERIMENT | $14_C$ cpm/mucosa | Bacteria/ mg $\times 10^3$ | $14_C$ cpm/mucosa | Bacteria/ mg $\times 10^3$ | $14_C$ cpm/mucosa | Bacteria/ mg $\times 10^3$ |
| 1 | 321.0 | 1.3 | 310.0 | 2.0 | 1182.6 | 10.3 |
| 2 | 812.0 | 1.8 | 1015.0 | 2.1 | 6008.0 | 8.2 |
| 3 | 188.7 | 0.7 | 3014.0 | 3.1 | 3422.0 | 3.2 |
| 4 | 1050.7 | 3.1 | 7340.0 | 20.6 | 52606.0 | 171.6 |
| 5 | 24607.0 | 55.5 | 20305.0 | 43.1 | 65228.0 | 2458.3 |
| 6 | 2054.0 | 6.7 | 7585.0 | 42.5 | 24819.0 | 136.9 |
| 7 | 101.5 | 0.8 | 1344.0 | 6.9 | 5651.0 | 41.2 |
| 8 | 1441.3 | 5.7 | 9155.0 | 28.9 | 46692.0 | 239.1 |

TABLE II

| BACTERIAL ADHERENCE TO ACID TREATED BLADDERS COMPARED TO CSA TREATED BLADDERS | | |
|---|---|---|
| | Bact./mg $\times 10^3$ ± S.D. | n |
| Acid/control | 22.72 ± 27.03 | 31 |
| 50 mg/ml CSA/control | 5.59 ± 4.9 | 25 |

TABLE III

| MANN WHITNEY RANK SUM TEST. NORMAL DEVIATE AND P VALUE OF THE COMPARISON OF BACTERIAL ADHERENCE TO ACID TREATED VS. CSA TREATED BLADDER WALLS | | |
|---|---|---|
| | Normal Deviate | P Value |
| Acid/Control versus 50 mg/ml CSA/Control | 2.695 | 0.007 |

The data in Table I shows that CSA is effective in inhibiting bacterial adherence to the bladder surface which has previously had the mucin layer removed, prevent bacterial infections during or following instrumentation whether surgical, diagnostic or post-operative; however, the invention is particularly useful in its ability to recoat the mucin layer of the urinary tract in post-menopausal women who are most prone to urinary tract infections secondary to hormonally related depletion of the natural mucin coat of the urinary tract.

THE EFFECTS OF CHONDROITIN-4-SULFATE ON TUMOR CELL IMPLANTATION

The five-year survival rate of patients with superficial bladder cancer ranges from 63–82%. There is, however, a 50–70% incidence of subsequent tumors. This rate is consistent in numerous series. There are probably two separate etiologies for this high incidence. (1) Histologic mapping of the bladder following cystectomy for invasive bladder cancer has demonstrated multifocal carcinoma or carcinoma in situ (CIS) in approximately 80% of specimens. This suggests that in patients with superficial tumors, most of the new tumor occurrences arising at sites distant from an original tumor are a consequence of continued growth of urothelial atypia or CIS. Further evidence for this multifocal "field change" comes from studies in which mucosal biopsies have been obtained from normal appearing mucosa at sites distant from evident tumor. The incidence of atypia, CIS, or cancer ranges from 20-80%. (2) The second explanation for the high incidence of subsequent tumors may be the implantation of tumor cells at the time of local resection or fulguration of tumor recurrences. Urothelial trauma during endoscopy may also provide a fertile site for viable tumor cells to implant and grow. Laboratory studies in animals and circumstantial evidence in man have provided evidence that this may account for some of the recurrences.

The technique that we have utilized to alter the urothelial surface in order to document that implantation will occur as well as to provide an experimental model has been the use of cautery or fulguration of the murine bladder. We have been able to reproducibly fulgurate the posterior portion of the mouse bladder. This technique best simulates what occurs in the urologic setting when the endoscopist fulgurates or resects a superficial bladder tumor.

Since the previous studies have provided experimental animal data that implantation does occur on the traumatized urothelial surface and there is circumstantial evidence in the human that implantation occurs following resection of the bladder tumor, a substance which might coat the urothelial surface or the tumor cells themselves might prevent this implantation from occurring. CSA may indeed have this particular property and the following study was performed in order to test this hypothesis.

METHODS

Animals

One hundred and thirty C3H/He female mice eight to ten weeks old were used.

Tumor cell

The tumor used in this study is the MBT-2 poorly differentiated transitional cell carcinoma. This tumor originated as an invasive neoplasm in a female C3H/He mouse which had ingested the carcinogen FANFT for eleven months. This tumor has been serially transplanted in syngeneic mice and was used in its 50th transplant generation. A single cell suspension of this tumor was prepared at the appropriate time by trypsin enzymatic dissociation.

Technique of cautery

In order to reproducibly perform the cauterization of the mouse bladder, animals were anesthetized and an insulated electrode consisting of 4-0 surgical wire insulated with a PE10 polyethylene tubing was inserted transurethrally. The tip of the wire was placed beyond the polyethylene tubing and positioned in contact with the posterior bladder wall. A Bovie unit was used to supply the electric current and was set at approximately 0.23 volts on 44 mAMPS. The charge was applied for approximately five seconds. Mice were kept in the prone position during this procedure and placed on a grounding plate.

The 130 mice were randomly divided into five groups of 26 aminals. Group I served as a control group and received saline intravesically. Groups II-V received the following drugs per the transurethral route: Heparin, 100 units/ animal, 5% CSA, 10% CSA, and 15% CSA.

The solutions were administered per urethra through a small urethral catheter and the drugs were instilled transurethrally on the first day of the experiment. They were instilled immediately after the cauterization. On Day 2 the mice were anesthetized and a second dose of the designated drugs was administered transurethrally. Immediately following the appropriate drug, a single cell suspension of $1.83 \times 10$ MBT-2 cells was placed.

Following the tumor cell instillation, the mice were followed and sacrificed four weeks later. After sacrifice, the bladder was distended with 10% Formalin, excised, and bisected to inspect for tumor. All bladders were examined grossly under an American optical stereoscope for tumor incidence. Histologic documentation was utilized if there was a question about the presence of tumor.

The control group which received intravesical irrigation with saline immediately prior to instillation of tumor cells had a tumor incidence of 44% (11/25). The only group having a substantial reduction in tumor incidence were those who received 15% CSA. The tumor incidence in this high dose CSA group was 4/22 (18%). There did appear to be a dose response curve for the group receiving CSA with the mice pretreated with 5 or 10% CSA having a subsequent tumor incidence of 35 and 30% respectively.

DISCUSSION

Urologists have often commented on the frequency of subsequent tumors particularly at the vesical neck or in the bladder dome following transurethral resection of superficial bladder cancer. They have implicated trauma from the procedure as a potential cause. There indeed is circumstantial evidence regarding the difference in location of secondary compared to initial tumors. Recurrent tummors occur in the dome not infrequently. However, this site is uncommon as the location of initial tumors. This indeed suggests that implantation may be a factor in tumor recurrence.

A technique which would coat the urothelial surface following cauterization may be extremely helpful in preventing the ability of these circulating tumor cells to implant and establish growth. CSA might possibly serve in this capacity. The study which we have performed indicates that CSA is capable of reducing the incidence of tumors which could only result by implantation of the instilled syngeneic transitional cell carcinoma cells. The lower tumor incidence in the various groups receiving 5% and 10% CSA was not significantly different from the control group although those receiving 15% had less than one-half the number of tumors, 18% vs. control 44%.

Having fully described the invention, it is intended that it be limited only by the lawful scope of the appended claims.

I claim:

1. The method which comprises the administration of "active" chondroitin sulfate A (CSA), "active" chondroitin sulfate C (CSC), or mixtures thereof to mammals including humans to the surfaces of the kidney, renal pelvis, ureter, bladder, urethra and related transitional cell surfaces by the irrigation of said surface with a solution of said drugs or mixtures thereof.

2. The method of claim 1 wherein the drug is administered in an effective amount as an aqueous solution.

3. The method of claim 1 wherein said drug is "active" chondroitin sulfate A (CSA).

4. The method of claim 1 wherein said drug is "active" chondroitin sulfate C (CSC).

5. The method of claim 1 wherein the irrigation mitigates against adhesion of E-Coli to the bladder surfaces.

6. The method of claim 1 wherein the irrigation mitigates against the incidence of transitional cell carcinoma in the bladder.

* * * * *